United States Patent [19]

Cassidy et al.

[11] 4,241,074
[45] Dec. 23, 1980

[54] PROSTAGLANDIN ANALOGUES

[75] Inventors: Frederick Cassidy; Alexander C. Goudie, both of Harlow, England

[73] Assignee: Beecham Group Limited, Great Britain

[21] Appl. No.: 48,514

[22] Filed: Jun. 14, 1979

[30] Foreign Application Priority Data

Jun. 15, 1978 [GB] United Kingdom ............... 27019/78

[51] Int. Cl.$^3$ .................. C07D 233/40; A61K 31/415
[52] U.S. Cl. ............................... 424/273 R; 548/312; 548/313; 548/309
[58] Field of Search ............... 548/313, 337, 309, 312, 548/313, 301; 424/273 R

[56] References Cited

U.S. PATENT DOCUMENTS 4,147,796  4/1979  Wooton ................................. 548/313

FOREIGN PATENT DOCUMENTS 2724948 12/1977 Fed. Rep. of Germany ........... 543/313

Primary Examiner—Henry R. Jiles
Assistant Examiner—Robert T. Bond
Attorney, Agent, or Firm—Jacobs & Jacobs

[57] ABSTRACT

A compound of the formula (I):

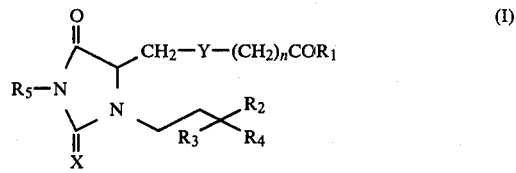

wherein:
X is O, S or H;
Y is —$CH_2$—CH—, —CH=CH— or —C≡C—;
n is 1 to 7;
$R_1$ is $C_{1-4}$ alkyl;
$R_3$ is hydroxy or protected hydroxy;
$R_4$ is $C_{1-9}$ alkyl, $C_{3-8}$ cycloalkyl or $C_{3-8}$ cycloalkyl—$C_{1-6}$ alkyl; or
$R_2$ and $R_4$ taken with the carbon atom to which they are joined represent a $C_{5-8}$ cycloalkyl group; and
$R_5$ is hydrogen or $C_{1-6}$ alkyl; and salts thereof has useful pharmaceutical activity including bronchodilator activity.

40 Claims, No Drawings

PROSTAGLANDIN ANALOGUES

This invention relates to novel compounds having pharmacological activity, to a process for their preparation, to intermediates useful in that process and to pharmaceutical compositions containing them.

German Offenlegungsschrift No. 2724948 discloses that compounds of the general formula (A);

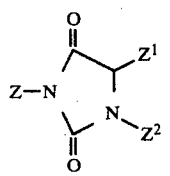

wherein Z is hydrogen or alkyl; one of $Z^1$ and $Z^2$ is a group $-CH_2-X-X^1-X^2$ in which X is phenylene, $-C\equiv C-$, cis- or trans- $-CH=CH-$ or $-CH_2-CQ_2-$, where each radical Q independently of the other is hydrogen or alkyl or the two radicals Q together are $C_{4-6}$ alkylene, $X^1$ is a covalent bond or a straight or branched $C_{1-6}$ alkylene chain, in which one methylene group is optionally substituted by an oxa ($-O-$) group, with the proviso that at least one carbon atom separates the oxa group from a $-C\equiv C-$, $-CH=CH-$ or CO group, and $X^2$ is tetrazolyl, carboxyl, carboxamide, hydroxymethylene or alkoxycarbonyl; and the other one of $Z^1$ and $Z^2$ is a group $-Y-Y^1-Y^2-Y^3$ in which Y is $-CR_2-CH_2-$, where each radical R independently of the other is hydrogen or methyl, $Y^1$ is carbonyl, methylene, methylene substituted by a hydroxy group or methylene substituted by a hydroxy and alkyl group, $Y^2$ is a covalent bond or straight-chain or branched $C_{1-7}$ alkylene optionally substituted on the carbon atom adjacent to $Y^1$ by one or two mutually independent alkyl, bicycloalkyl or cycloalkyl groups, $Y^3$ is hydrogen, hydroxy, $C_{1-7}$ (preferably $C_{1-4}$) alkoxy, cycloalkyl, bicycloalkyl, phenyl, benzyl, phenoxy or benzyloxy, where each phenyl, benzyl, phenoxy or benzyloxy group may be substituted in the benzene ring by one or more hydroxy, halogen, nitro, amino, acylamino, alkenyl, alkoxy, phenyl or alkyl groups, which themselves may be substituted by one or more halogens or Y is a bond, $-CH_2-$ or $-CH_2.CH_2-$ and $Y^1$, $Y^2$ and $Y^3$ together are cycloalkyl which is substituted by a hydroxy group which is preferably separated by 3 carbon atoms from the hydantoin ring, have similar pharmacological activity to natural prostaglandins.

We have now discovered a class of compounds which have useful pharmocological activity and which are structurally distinct from the compounds disclosed in Offenlegungsschrift No. 2724948.

This class of compounds of this invention is structurally distinct from the compounds of formula (B):

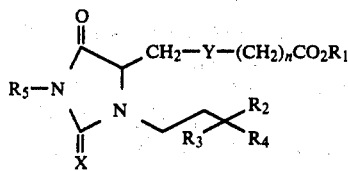

wherein:

X is O to S;
n is 1 to 8;
$R_1$ is hydrogen, or $CO_2R_1$ represents an ester group in which the $R_1$ moiety contains from 1-12 carbon atoms;
$R_2$ is hydrogen, $C_{1-4}$ alkyl, or phenyl;
$R_3$ is hydroxy or protected hydroxy;
$R_4$ is hydrogen, $C_{1-9}$ alkyl, $C_{3-8}$ cycloalkyl, $C_{3-8}$ cycloalkyl-$C_{1-6}$ alkyl, phenyl, phenyl $C_{1-6}$ alkyl, naphthyl, naphthyl-$C_{1-6}$-alkyl, any of which phenyl or naphthyl moieties may be substituted by one or more halogen, trifluoromethyl, $C_{1-6}$ alkyl, hydroxy, $C_{1-6}$ alkoxy, phenyl $C_{1-6}$ alkoxy or nitro groups; or
$R_2$ and $R_4$ taken with the carbon atom to which they are joined represent a $C_{5-8}$ cycloalkyl group;
$R_5$ is hydrogen, $C_{1-6}$ alkyl, $C_{1-6}$ alkyl substituted by a nitro, hydroxy, $C_{1-6}$ alkoxy, $CO_2A$, $(CO_2A)_2$, CN or halogen group, $C_{5-8}$ cycloalkyl, phenyl, phenyl-$C_{1-6}$ alkyl, phenyl-$C_{3-6}$ cycloalkyl, any of which phenyl moieties may be substituted with one or more halogen, trifluoromethyl, $C_{1-6}$ alkyl, $C_{1-6}$ alkoxy or nitro groups; or a group $CO_2A$; in $R_5$ when present A is hydrogen or $CO_2A$ represents an ester group in which the A moiety contains from 1 to 12 carbon atoms; and salts thereof; which are disclosed in our West German Offenlgungsschrift No. 2755771 as having useful prostaglandin-like activity. It should be noted that West German Offenlgungsschrift No. 2755771 published after the date of filing of the priority application for this invention.

Accordingly the present invention provides a compound of formula (I):

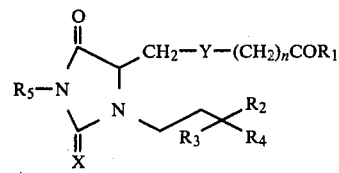

wherein:
X is O, S or $H_2$;
Y is $-CH_2-CH_2-$, $-CH=CH-$ or $-C\equiv C-$;
n is 1 to 7;
$R_1$ is $C_{1-4}$ alkyl;
$R_2$ is hydrogen or $C_{1-4}$ alkyl;
$R_3$ is a hydroxy or protected hydroxy;
$R_4$ is $C_{1-9}$ alkyl, $C_{3-8}$ cycloalkyl or $C_{3-8}$ cycloalkyl-$C_{1-6}$ alkyl; or
$R_2$ and $R_3$ taken with the carbon atom to which they are joined represent a $C_{5-8}$ cycloalkyl group; and
$R_5$ is hydrogen or $C_{1-6}$ alkyl; and salts thereof.

One class of compounds within formula (I) are those as defined but wherein n is 1 to 5. Preferably n is 3, 4 or 5, most preferably 4.

Particularly suitable compounds within formula (I) include those where X is O.

Suitable examples of $R_1$ include methyl and ethyl.

Suitable examples of $R_2$ include hydrogen, methyl and ethyl. More suitably $R_2$ is hydrogen or methyl, preferably methyl.

Suitable protected hydroxyl groups $R_3$ include readily hydrolysable groups such as acylated hydroxy groups in which the acyl moiety contains 1 to 4 carbon atoms, for example the acetoxy group; and hydroxy groups etherified by readily removable inert groups such as the benzyl group or like groups. Preferably $R_3$ is hydroxyl.

Suitable groups $R_4$ when $R_4$ is an alkyl group include $C_{4-9}$ alkyl groups. Such $C_{4-9}$ alkyl groups may be straight chain alkyl groups, such as n-butyl, n-pentyl, n-hexyl and n-heptyl, or may be alkyl groups branched by one or two methyl groups (at the same or different carbon atoms). Thus for example, $R_4$ may be a group $CH_2R_7$, $CH(CH_3)R_7$ or $C(CH_3)_2R_7$, wherein $R_7$ is a straight chain alkyl group such that the carbon content of the resultant group $R_4$ is 4 to 9.

In general preferred groups $R_4$ when $R_4$ is an alkyl group include straight chain pentyl, hexyl and heptyl groups. Of these, straight chain hexyl is often the most useful. Other preferred groups $R_4$ include groups $CH(CH_3)R_7$ and $C(CH_3)_2R_7$ wherein $R_7$ is straight chain butyl, pentyl and hexyl.

Other suitable examples of $R_4$ when $R_4$ is an alkyl group include the lower alkyl groups, that is when $R_4$ is a $C_{1-4}$ alkyl group.

When $R_4$ is or contains a $C_{3-8}$ cycloalkyl moiety, the moiety may be cyclopropyl. The moiety may also be a $C_{5-8}$ cycloalkyl moiety such as a cyclohexyl moiety. Examples of suitable $C_{1-6}$ alkyl moieties when $R_4$ is a $C_{3-8}$ cycloalkyl-$C_{1-6}$ alkyl group include methyl, ethyl, propyl, butyl and pentyl.

Also $R_2$ and $R_4$ taken with the carbon atom to which they are joined can represent a $C_{5-8}$ cycloalkyl groups, such as the cyclohexyl group.

Suitable examples of $R_5$ include hydrogen, methyl, ethyl, n- and iso-propyl, n-, sec- and tert-butyl. More suitably $R_5$ is hydrogen or methyl, preferably methyl.

The compounds of the formula (I) may form conventional salts. Such salts include those with alkali and alkaline earth metals, suitably sodium and potassium, and ammonium and substituted ammonium salts, and acid addition salts when X is $H_2$.

From the aforesaid it will be seen that one particularly suitable group of compounds within formula (I) is of formula (II):

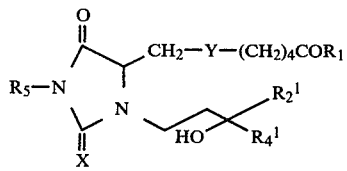

wherein:
X, Y, $R_1$ and $R_5$ are as defined in formula (I);
$R_2^1$ is hydrogen, methyl or ethyl;
$R_4^1$ is $C_{1-9}$ alkyl; and salts thereof.
In formula (II) suitably X is O.
Suitably $R_1$ is methyl.
$R_2^1$ is more suitably hydrogen or methyl, preferably methyl.

While $R_4^1$ may be a $C_{1-9}$ alkyl group, it is normally a $C_{4-9}$ alkyl group. In such cases suitable and preferred straight chain and branched groups $R_4^1$ include those previously described as suitable and preferred for the group $R_4$ when $R_4$ is a $C_{4-9}$ alkyl group. Such preferred groups $R_4^1$ include straight chain pentyl, hexyl, and heptyl and of these normally the most useful is straight chain hexyl. Other preferred groups $R_4^1$ include $CH(CH_3)R_7^1$ and $C(CH_3)_2R_7^1$ wherein $R_7^1$ is straight chain butyl, pentyl or hexyl.

Suitably $R_5$ is methyl or ethyl, preferably methyl.

A further group of compounds within formula (I) of interest is of formula (III):

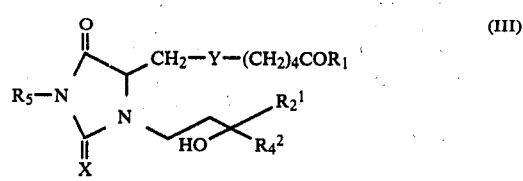

wherein:
X, Y, $R_1$ and $R_5$ are as defined in formula (I):
$R_2^1$ is hydrogen, methyl or ethyl;
$R_4^2$ is a group of formula (IV):

wherein
T is a bond, or a $C_{1-6}$ alkylene group which may be straight chain or branched by one or two methyl groups at the same or different carbon atoms; and
r is 0 to 3;
and salts thereof.
In formula (III) suitably X is O.
Suitably $R_1$ is methyl.
$R_2^1$ is more suitably hydrogen or methyl, preferably methyl.

In formula (IV) often T will be a group $-(CH_2)_q-$ wherein q is 0 to 4. Also suitably r is 1.

Suitably $R_5$ is methyl or ethyl, preferably methyl.

It will of course be realised that the compounds of the formula (I) have asymmetric centres, and thus are capable of existing in a number of stereoisomeric forms. The invention extends to each of these stereoisomeric forms, and to mixtures thereof. The different stereoisomeric forms may be separated one from the other by the usual methods.

The present invention further provides a process for the preparation of the compounds of the formula (I) which process comprises the cyclisation of a compound of formula (V):

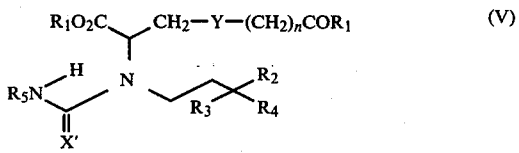

wherein the variable groups are as defined and X' is O or S; and thereafter if desired or necessary converting X, Y, $R_3$ and $R_5$ in the thus formed compound into other variables X, Y, $R_1$, $R_3$ and $R_5$.

When $R_5$ is alkyl in the compound of formula (V), then the compound of the formula (V) is conveniently prepared in situ during the reaction of a compound of the formula (VI):

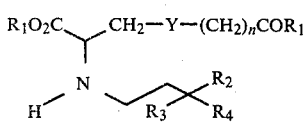 (VI)

with $R_5 NCX^1$ wherein $R_5$ is alkyl and $X^1$ is O or S.

This preferred process is suitably carried out under reflux in an inert solvent such as benzene and the like. It should be stated that when in this reaction $R_5$ is a sterically hindered group then this reaction may proceed only as far as the uncyclised compound of formula (V), in which case the necessary cyclisation of the compound (V) can be achieved with a strong base, such as sodium hydride or sodium ethoxide, in a dry organic solvent. Sodium ethoxide in benzene, or potassium t-butoxide in toluene, benzene or hexamethyl phosphoramide are suitable reagents.

When $R_5$ is hydrogen in the compound of formula (V), then the compound of formula (V) is conveniently formed in situ during the reaction of a compound of formula (VI) with a salt $M^+\overline{C}NX^1$ wherein $M^+$ is a metal ion, preferably potassium, in the presence of acid. The acid for this reaction, which yields a compound of the formula (I), is suitably provided by using an acid addition salt of the compound of formula (VI), or by carrying our the reaction in aqueous acid.

The conversion of a compound of the formula (I) to another compound of the formula (I) wherein X, Y, $R_3$ and/or $R_5$ are altered, when desired or necessary, may be achieved in any convenient manner.

For example compounds wherein X is S may be converted to compounds wherein X is $H_2$ by reduction. This reductive desulphurisation may be carried out in the presence of a suitable conventional hydrogenation catalyst, such as Raney nickel, under conventional conditions for such reactions. For example a solution of the chosen compound of the formula (I) wherein X is S in an organic solvent may be added to a refluxing suspension of the catalyst in a similar solvent.

Also for example if desired compounds wherein Y is —C≡C— may be reduced to compounds wherein Y is —CH=CH— in known manner. Suitably this reaction is carried out using catalytic hydrogenation, such as Lindlar catalysis. When Y is —CH=CH—, it may be reduced to —CH$_2$—CH$_2$— in known manner, suitably using catalytic hydrogenation such as transition metal catalysis.

Similarly protected $R_3$ hydroxy moieties may be de-protected in conventional manner. For example when $R_3$ is a benzyloxy group, the benzyl group may readily be removed by hydrogenolysis. Thus it may be seen that 'protected hydroxy' compounds of the formula (I) are useful intermediates in the preparation of the corresponding 'free hydroxy' compounds of the formula (I).

Also when a compound of the formula (I) contains an acidic hydrogen atom(s), salts thereof may be prepared in conventional manner for example by reacting the compound of the formula (I) with the required base. For salts of compounds wherein $R_5$ is hydrogen, the base should be a strong base such as for example sodium in an alcohol, such as ethanol, or the like.

Also $R_5$ is hydrogen compounds of the formula (I) may be converted to corresponding compounds but wherein $R_5$ is alkyl by conventional substituted reactions with $R_5L$ wherein L is a displaceable group such as a halide or other good leaving group. In such reactions it may be necessary to first convert the compound of the formula (I) to an alkali metal salt of the $R_5$ hydrogen.

Compounds of formula (VI) may be prepared by reacting a compound of formula (VII): $H_2NCH_2CH_2CR_2R_3R_4$ with a compound of formula (VIII): $R_1O_2C$—CH(Q)—CH$_2$—Y—(CH$_2$)$_n$COR$_1$, wherein the variable groups are as defined and Q is a good leaving group.

Suitably Q is tosylate of a halide, or like readily displaceable group. Preferably Q is bromide.

This displacement reaction occurs under conventional conditions, for example in an organic solvent in the presence of a base. The reaction may suitably be carried out in hexamethylphosphoramide in the presence of sodium carbonate and sodium iodide at ambient temperature or below.

Compounds of formula (VII) may be prepared in known manner.

Compounds of formula (VIII) may suitably be prepared by de-acylation of a corresponding compound of the formula (IX):

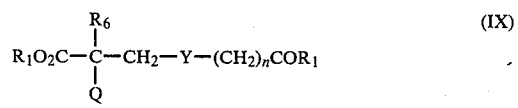 (IX)

wherein $R_6$ is an acyl group containing up to 6 carbon atoms (preferably acetyl).

This de-acylation can conveniently be carried out by reaction with a suspension of anhydrous barium hydroxide in alcohol.

Compounds of the formula (IX) may be prepared by substitution of a corresponding compound of the formula (X):

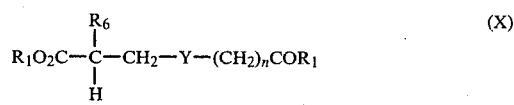 (X)

with a good leaving group.

This reaction is suitably carried out in an organic solvent such as tetrahydrofuran in the presence of a strong base such as sodium hydride. When Q is bromide in the desired compound of formula (IX), the reaction is suitably carried out with bromine dissolved in a suitable organic solvent such as dichloromethane, at ambient temperature or below.

Compounds of formula (X) may be prepared from compounds of the formula (XI): $R_1O_2C$—CH$_2$—R$_6$ by alkylation thereof with a compound of formula (XVI): Q—CH$_2$—Y—(CH$_2$)$_n$COR$_1$.

This alkylation reaction can be carried out in conventional manner, for example in an organic solvent in the presence of a strong base such as sodium hydride.

It is believed that compounds of the formula (VI) are novel, and thus form part of this invention as novel intermediates.

Compounds within the formula (I) have particularly useful pharmacological activity. For example compounds within the formula (I) have anti-gastric secretion activity, anti-ulcer activity, cardiovascular activity, e.g. anti-hypertension activity, platelet aggregation inhibition activity, affect the respiratory tract, e.g. bronchodilator activity, and have anti-fertility, smooth muscle and anti-arrhythmic activity. Thus compounds of the formula (I) may be used in the treatment or prophylaxis of corresponding disorders in humans and animals.

In general it may be said that compounds within the formula (I) have a range of pharmcological activities similar to those shown by the natural prostaglandins, but that these activities tend to be rather more selective.

The compounds of the formula (I) have especially useful bronchodilation activity.

The invention therefore also provides a pharmaceutical composition comprising a compound of the formula (I) and a pharmaceutically acceptable carrier.

The compounds of the formula (I) also have good stability.

Clearly the formulation of the said pharmaceutical composition will depend on the nature of the activity shown by the chosen compound of the formula (I), and on other factors such as a preference in a particular area of therapy for a particular mode of administration.

The composition may be in the form of tablets, capsules, powders, granules, lozenges or liquid preparations, such as oral or sterile parenteral solutions or suspension.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, emulsions, syrups or elixirs, or may be presented as a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For parenteral administration, fluid unit dosage forms are prepared utilising the compound of the formula (I) and a sterile vehicle. The compound, depending on the vehicle and concentration used, can be either suspended or dissolved in the vehicle. In preparing solutions the compound can be dissolved for injection and filter sterilised before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously a surfactant or wetting agent is included in the composition to facilitate uniform distribution of the compound.

When appropriate, the compositions of this invention may be presented as an aerosol for oral administration, or as a microfine powder for insufflation.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention also provides a method of treatment and/or prophylaxis of disorders in human being or animals which comprises the administration to the sufferer of an effective amount of a compound of the formula (I). Normally however the compounds will be used in the therapy of human disorders.

The following Examples illustrate the preparation of compounds of the formula (I) and their pharmacological properties.

EXAMPLE 1 (a)

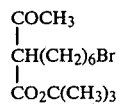

A solution of t-butyl acetoacetate (12.64 g) in dry tetrahydrofuran (25 ml) was added dropwise to a cooled suspension of sodium hydride (3.0 g, 80% dispersion) in dry tetrahydrofuran (50 ml). The mixture was stirred under nitrogen and, when effervescence ceased, the solution was refluxed for 30 minutes.

After cooling, sodium iodide (ca. 1 g) was added and a solution of 1,6-dibromohexane (39.04 g, 2 equivalents) was run in. The mixture was refluxed overnight with stirring under nitrogen.

The reaction mixture was diluted with water and extracted with ether. The etheral solution was washed with brine, dried over magnesium sulphate and evaporated to give a yellow liquid. The product was fractionally distilled to give t-butyl 2-acetyl-8-bromo-octanoate as a colourless liquid (13.3 g), b.p. 140°–150°/0.2 mm Hg.

EXAMPLE 1 (b)

A solution of t-butyl 2-acetyl-8-octanoate (9.0 g) and toluene p-sulphonic acid (420 mg) in xylene (30 ml) was refluxed with stirring for 5 hours.

The solvent was evaporated and the residue taken up in ether. The ethereal solution was washed with sodium bicarbonate solution and with brine, dried over magnesium sulphate and evaporated to give an orange liquid.

The product was fractionally distilled to give 9-bromo-nonan-2-one as a colourless liquid (4.4 g), b.p. 108°/0.15 mm Hg.

EXAMPLE 1 (c)

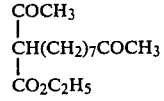

A solution of ethyl acetoacetate (16.04 g) in dry tetrahydrofuran (50 ml) was added dropwise to a cooled suspension of sodium hydride (3.73 g, 80% dispersion) in dry tetrahydrofuran (100 ml). The mixture was stirred under nitrogen and, when effervescence ceased, the solution was refluxed for 30 minutes.

After cooling, sodium iodide (ca. 1 g) was added and a solution of 9-bromo-nonan-2-one (27.3 g) in dry tetrahydrofuran (50 ml) was run in. The mixture was refluxed overnight with stirring under nitrogen.

The reaction mixture was diluted with water and extracted with ether. The ethereal solution was washed with brine, dried over magnesium sulphate and evaporated to give a yellow liquid. The product was fractionally distilled to give ethyl 2-acetyl-10-oxo-undecanoate as a colourless liquid (21.5 g), b.p. 156°/0.15 mm Hg.

EXAMPLE 1 (d)

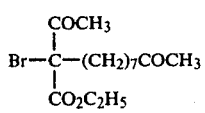

A solution of ethyl 2-acetyl-10-oxo-undecanoate (21.4 g) in dry tetrahydrofuran (50 ml) was added dropwise to a cooled suspension of sodium hydride (2.54 g, 80% dispersion) in dry tetrahydrofuran (100 ml). The mixture was stirred under nitrogen and, when effervescence ceased, the solution was refluxed for 30 minutes.

The mixture was cooled in an ice-salt bath and a solution of bromine (4.34 ml) in dichloromethane (25 ml) was run in rapidly. The solution was allowed to warm to room temperature.

The reaction mixture was diluted with water and extracted with ether. The ethereal solution was washed with brine, dried over magnesium sulphate and evaporated in vacuo at room temperature to give ethyl 2-acetyl-2-bromo-10-oxo-undecanoate as a brownish oily liquid (28.8 g), which was used immediately without further purification.

EXAMPLE 1 (e)

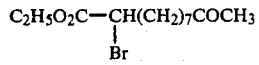

anhydrous barium hydroxide (7.38 g) was added to a cooled solution of ethyl 2-acetyl-2-bromo-10-oxo-undecanoate (28.8 g) in dry ethanol (250 ml) and the mixture was stirred at room temperature overnight.

The reaction mixture was filtered and the filtrate evaporated. The residue was extracted with ether and the ethereal solution was washed with brine, dried over magnesium sulphate and evaporated to give a yellow liquid. The product was fractionally distilled to give ethyl 2-bromo-10-oxo-undecanoate as a pale yellow liquid (8.8 g), b.p. 155°–162°/0.6 mm Hg, containing a trace impurity.

EXAMPLE 1 (f)

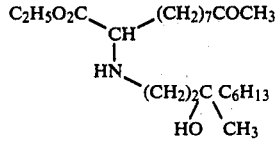

Ethyl 2-bromo-10-oxo-undecanoate (8.75 g) in dry ethanol (40 ml) was added dropwise to a refluxing solution of 3-hydroxy-3-methyl-nonyl amine (7.39 g, 1.5 equivalents) in dry ethanol (100 ml), contaning a suspension of anhydrous sodium carbonate (4 g). The mixture was refluxed with stirring overnight.

The reaction mixture was filtered and the filtrate was evaporated. The residue was taken up in ether and the ethereal solution washed with brine until neutral, dried over magnesium sulphate and evaporated to give a yellow oily liquid. The product was purified by column chromatography, using chloroform as solvent, to give ethyl 2-(N-3-hydroxy-3'-methyl-n-nonyl) amino-10-oxo undecanoate as a colourless oil (5.35 g).

| I.R (cm$^{-1}$): | |
|---|---|
| | 3500 to 3200 [—OH,—N̶—H] |
| | 1730 [—CO$_2$C$_2$H$_5$] |
| | 1720 [CH$_3$CO—] |
| NMR (τ, CCl$_4$): | 7.96, (s), [CH$_3$CO—] |
| | 5.85, (q), [—CO$_2$CH$_2$CH$_3$] |

EXAMPLE 1 (g)

Compound 1 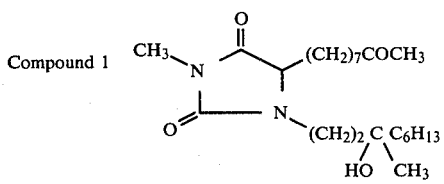

A solution of methyl isocyanate (250 mg) in dry toluene (25 ml) was added to a solution of ethyl 2-(N-3'-hydroxy-3'-methyl-n-nonyl)amino-10-oxo-undecanoate (1.47 g) in dry toluene (40 ml) at room temperature. The mixture was stirred for 10 minutes and then refluxed with stirring for 4 hours.

The solvent was evaporated and the residue was taken up in ether. The ethereal solution was washed with dilute hydrochloric acid and with brine, dried over magnesium sulphate and evaporated to give a colourless oily liquid.

The product was purified by column chromatography, using chloroform as solvent, to give 1-(3'-hydroxy-3'-methyl-n-nonyl)-3-methyl-5-(8"-oxo-n-nonyl) hydantoin as a colourless oil (1.35 g).

| I.R. (cm$^{-1}$): | 3450 [—OH]; 1765, 1700 |
|---|---|
| | 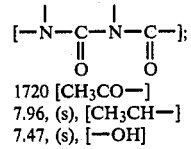 |
| | 1720 [CH$_3$CO—] |
| NMR (τ,CCl$_4$): | 7.96, (s), [CH$_3$CH—] |
| | 7.47, (s), [—OH] |
| | 7.11, (s), [—N̶—CH$_3$] |
| Mass spectrum: | C$_{23}$H$_{40}$N$_2$O$_3$[m*-H$_2$O] |
| requires: | 392.3039 |
| found: | 392.3028 |

EXAMPLE 2

Compound 2 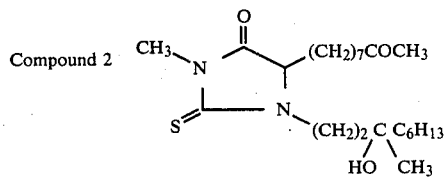

A solution of methyl isothiocyanate (0.70 g) in dry toluene (25 ml) was added to a solution of ethyl 2-(N-3'-hydroxy-3'-methyl-n-nonyl) amino-10-oxo-undecanoate (3.75 g) in dry toluene (75 ml) at room temperature. The mixture was stirred for 10 minutes and then refluxed with stirring for 3 hours.

The solvent was evaporated to give a colourless oil, which was purified by column chromatography, using chloroform as solvent, giving 1-(3'-hydroxy-3'-methyl-n-nonyl)-3-methyl-5-(8"-oxo-n-nonyl)-2-thiohydantoin as a colourless oil (1.36 g).

| I.R. (cm$^{-1}$): | 3475 [—OH]; 1740, 1715 |
| --- | --- |
| | $[-\underset{\underset{S}{\parallel}}{N}-\underset{}{C}-\underset{}{N}-\underset{\underset{O}{\parallel}}{C}-, CH_3CO-]$ |
| NMR (τ, CCl$_4$): | 7.95, (s), [CH$_3$CO—] |
| | 7.88, (s), [—OH] |
| | 6.83, (s), [—N—CH$_3$] |
| Mass spectrum: | C$_{23}$H$_{40}$N$_2$O$_2$S [m*-H$_2$O] |
| requires: | 408.2811 |
| found: | 408.2798 |

EXAMPLE 3

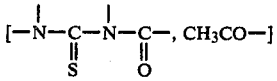

Compound 3

NICAT 101 (ca. 20 g) was washed with methanol (×3) and transferred to a 250 ml 3-necked flask. The methanolic suspension was stirred and gently refluxed. A solution of 1-(3'-hydroxy-3'-methyl-n-nonyl)-3-methyl-5-(8"-oxo-n-nonyl)-2-thiohydantoin (2.7 g) in methanol (20 ml) was run in slowly and refluxing continued for 20 minutes.

The reaction mixture was filtered hot and the residue washed with methanol. The filtrate was evaporated to give a pale yellow oil, shown by thin layer chromatography to be a mixture of product and starting material.

The experiment was repeated on the recovered material to give a yellow oil, which was purified by column chromatography, using chloroform as solvent, to give 1-(3'-hydroxy-3'-methyl-n-nonyl)-3-methyl-5-(8"-oxo-n-nonyl)-4-imidazolidone as a colourless oil (700 mg).

| I.R. (cm$^{-1}$): | 3420 [—OH]; 1710 [—N—C—, |
| --- | --- |
| | $\quad\quad\quad\quad\quad\quad\quad\quad\quad\quad\quad\quad\quad\quad\quad\quad\parallel$ |
| | $\quad\quad\quad\quad\quad\quad\quad\quad\quad\quad\quad\quad\quad\quad\quad\quad O$ |
| | CH$_3$CO—] |
| NMG (τ, CCl$_4$): | 7.96, (s), [CH$_3$CO—] |
| | 7.18, (s), [—N—CH$_3$] |

EXAMPLE 4

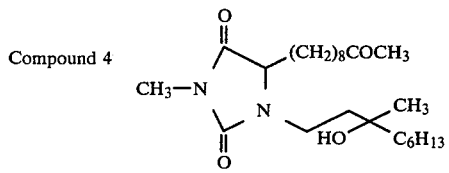

Compound 4

In a similar manner to that of example 1 (g), compound 4, 1-(3'-hydroxy-3'-methyl-n-nonyl)-3-methyl-5-(9"-oxo-n-decyl) hydantoin was prepared using ethyl 2-(3'-hydroxy-3'-methyl-n-nonyl) amino-11-oxo-duodecanoate and methyl isocyanate.

| I.R. | 3450, [OH]; 1765, |
| --- | --- |
| film (cm$^{-1}$) | $\quad\quad\quad\quad O\quad\quad O\,O$ |
| | $\quad\quad\quad\quad\parallel\quad\quad\parallel\,\parallel$ |
| | 1705[N—C—N—C; CCH$_3$]. |
| N.M.R. | |
| (τ,CDCl$_3$): | 7.85, s, 3H, [COCH$_3$]; |
| | 7.55, t, 2H, [CH$_2$COCH$_3$]; |
| | 7.0, s, 3H, [NCH$_3$]; |
| | 6.95, s, 1H, [OH]; |
| | 6.5, brm, 2H, [NCH$_2$]; |
| | 6.95, m, 1H, [NCH]. |
| Mass Spec: C$_{24}$H$_{44}$N$_2$O$_4$ (M*) | requires 424.3298 |
| | found 424.3299. |

EXAMPLE 5 (a)

CH$_3$SO$_2$OCH$_2$CH=CH(CH$_2$)$_4$COCH$_3$

Methane sulphonylchloride (8.07 g; 1.1 eq) was added dropwise over 30 minutes to a stirred solution of 9-hydroxy-non-7-en-2-one (10 g) in dry dichloromethane (60 ml) containing an excess of triethylamine (9.71 g; 1.5 eq), at −10° C. The solution was stirred for a further 20 minutes. The reaction mixture was washed with cold water, cold 5 N hydrochloric acid, cold 5% sodium bicarbonate solution and cold brine then was dried and evaporated in vacuo at <30° to give 9-mesyloxy-non-7-en-2-one (12.7 g) as a deep red oil.

In a similar manner, 9-mesyloxy-non-7-yn-2-one was prepared from 9-hydroxy-non-7-yn-2-one.

EXAMPLE 5 (b)

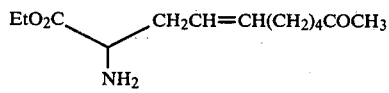

The N-benzilidine derivative of glycine ethyl ester (11.4 g; 1.1 mol. eq.) in dry tetrahydrofuran (30 ml) was added dropwise to a stirred slurry of potassium tert-butoxide (6.69 g; 1.1 mol. eq.) in dry tetrahydrofuran (20 ml) at −78° C. After a further 10 minutes, sodium iodide (0.81 g; 0.1 mol. eq.) was added and 9-mesyloxy-non-7-ene-2-one (12.7 g) in dry tetrahydrofuran (100 ml) was added dropwise. The resulting yellow mixture was stirred at −78° C. for 2 hours and then was allowed to gradually warm to room temperature. The mixture was stirred for a further 3 hours at room temperature and was then diluted with ether. The ether solution was washed with brine, dried and evaporated to give a red oil (23 g).

The ethyl 2-amino-10-oxo-undec-4-enoate (5.6 g) was obtained via column chromatography of the above N-benzylidine derivative on silica gel (460 g) using pentane; pentane, diethyl ether 9:1; pentane, diethyl ether 3:1; pentane diethyl ether 1:1; diethyl ether and diethyl ether, methanol 9:1 as eluants.

In a similar manner, ethyl 2-amino-10-oxo-undec-4-ynoate was prepared from 9-mesyloxy-non-7-yn-2-one.

EXAMPLE 5 (c)

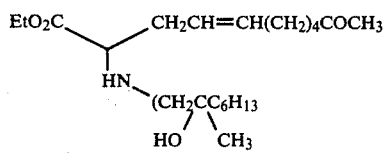

Ethyl 2-amino-10-oxo-undec-4-enoate (5.6 g), 1-para-toluene sulphonyloxy-3-methylnonan-3-ol (8.38 g), dry potassium carbonate (3.2 g) and sodium iodide (3.48 g) were stirred together in dry acetonitrile (200 ml) for 2 hours, under nitrogen. The reaction mixture was refluxed overnight, then was cooled and extracted into ether. The ether solution was washed with brine, dried and evaporated in vacuo to give a red oil (10 g) which was purified via column chromatography on silica gel (300 g) using ethyl acetate, hexane 1:3 and ethyl acetate, hexane 3:2 as eluants. Ethyl 2-(3'-hydroxy-3'-methyl-n-nonyl) amino-10-oxo-undec-4-enoate (3.3 g) was obtained as a pale yellow oil.

In a similar manner, ethyl 2-(3'-hydroxy-3'-methyl-n-nonyl) amino-10-oxo-undec-4-ynoate was prepared from ethyl 2-amino-10-oxo-undec-4-ynoate.

EXAMPLE 5 (d)

Compound 5

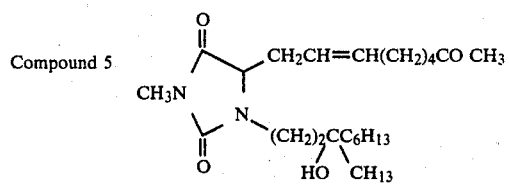

1-(3'-hydroxy-3'-methyl-n-nonyl)-3-methyl-5-(8''-oxo-non-2-enyl) hydantoin was prepared as in Example 1 (g) using ethyl 2-(3'-hydroxy-3'-methyl-n-nonyl) amino-10-oxo-undec-4-enoate and methyl isocyanate.

Analysis: $C_{23}H_{40}N_2O_4$ requires: C, 67.61; H, 9.87; N, 6.86%. found: C, 67.56; H, 9.92; N, 6.76%.

| I.R. (cm$^{-1}$) film: | 3450, [OH]; 1765, 1710 [N—C—N—C; CCH$_3$] with O, O O carbonyls |
|---|---|
| N.M.R. (τ, CCl$_4$): | 7.95, s, 3H, [COCH$_3$]; 7.65, brm, 6H, [CH$_2$COCH$_3$; CH$_2$CH=CH CH$_2$] 7.10, s, 3H, [NCH$_3$]; 6.5, brm, 2H, [NCH$_2$]; 6.0, m, 1H, [NCH]; 4.65, brm, 2H, [HC=CH]. |
| Mass Spec: $C_{23}H_{40}N_2O_4$ (M*) | requires: 408.2987 found: 408.2994. |

EXAMPLE 6

Compound 6

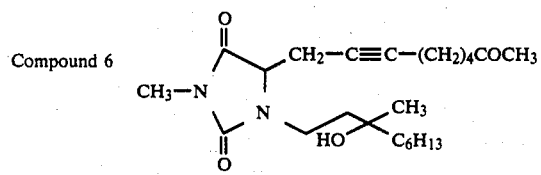

In a similar manner to that of Example 5 (d), Compound 6, 1-(3'-hydroxy-3'-methyl-n-nonyl)-3-methyl-5-(8''-oxo-non-2-ynyl) hydantoin was prepared from ethyl 2-(3'-hydroxy-3'-methyl-n-nonyl)amino-10-oxo-undec-4-ynoate and methyl isocyanate.

| I.R. (cm$^{-1}$) film: | 3450, [OH]; 1770, 1710 broad [N—C—N—C; COCH$_3$]. |
|---|---|
| N.M.R. (τ): | 7.9, s, 1H, [OH]; 7.85, s, 3H, [COCH$_3$]; 7.55, m, 4H, [CH$_2$COCH$_3$; C≡C CH$_2$]; 7.25, m, 2H, [CH$_2$C≡C]; 7.0, s, 3H, [NCH$_3$]; 6.6, brm, 2H, [NCH$_2$]; 5.95, t, 1H, [NCH]. |
| Mass Spec: $C_{23}H_{38}N_2O_4$ | requires: 406.2828 found: 406.2815. |

EXAMPLE 7

Compound 7

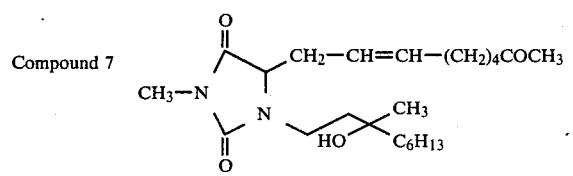

In a similar manner to that of Example 2, Compound 7 1-(3'-hydroxy-3'-methyl-n-nonyl)-3-methyl-5-(8''-oxo-non-2-enyl)-2-thiohydantoin was prepared from ethyl 2-(3'-hydroxy-3'-methyl-n-nonyl)amino-10-oxo-undec-4-enoate and methyl isothiocyanate.

Analysis: $C_{23}H_{40}N_2O_4S$ requires: C, 65.06; H, 9.49; N, 6.59; S, 7.55%. found: C, 65.18; H, 9.77; N, 6.55; S, 7.65%.

| I.R. (cm$^{-1}$) film: | 3470 [OH]; 1740, 1710 [N—C—N—C; CCH$_3$] with S, O O. |
|---|---|
| N.M.R. (τ, CCl$_4$): | 7.9, s, 3H, [COCH$_3$]; 7.7, brm, and 7.3,brm, 6H, [CH$_2$COCH$_3$; CH$_2$CH=CHCH$_2$]; 6.8, s, 3H, [NCH$_3$]; 6.55, brm, 2H, [NCH$_2$]; 5.85, m, 1H, [NCH]; 4.6, brm, 2H, [CH=CH]; |
| Mass Spec: $C_{23}H_{40}N_2O_4S$ (M*) | requires: 424.2759 found: 424.2777. |

EXAMPLE 7 (a)

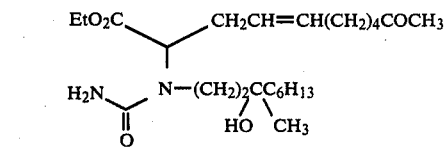

Potassium cyanate (0.26 g) in water (5 ml) was added dropwise to a stirred ice-cold, solution of ethyl 2-(3'-hydroxy-3'-methyl-n-nonyl)amino-10-oxo-undec-4-enoate (640 mg) in methanol (3.2 ml) containing 2 N hydrochloric acid (1.6 ml). The mixture was stirred at room temperature overnight. The methanol was evaporated at room temperature in vacuo and the residue was partitioned between water and ether. The ether solution was washed with brine, dried and evaporated in vacuo at room temperature to give ethyl 2-[N-(3'-hydroxy-3'-methyl-n-nonyl)-N-aminocarbonyl]amino-10-oxo-undec-4-enoate (500 mg) as a dark yellow gum.

In a similar manner, ethyl 2-[N-(3'-hydroxy-3'-methyl-n-nonyl)-n-aminocarbonyl]amino-10-oxo-undecanoate was prepared from ethyl 2-(3'-hydroxy-3'-methyl-n-nonyl)-amino-10-oxo-undecanoate.

EXAMPLE 7 (b)

Compound 7 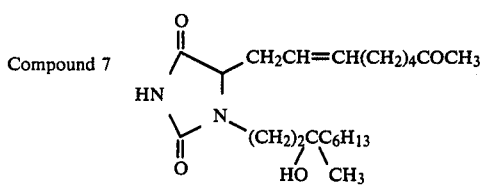

Ethyl 2-[N-(3'-hydroxy-3'-methyl-n-nonyl)-N-aminocarbonyl]amino-10-oxo-undec-enoate (500 mg) was heated at 100° C. for 5 hours to give 1-(3'-hydroxy-3'-methyl-n-nonyl)-5-(8''-oxo-non-2-enyl) hydantoin (460 mg) as a yellow gum.

| | |
|---|---|
| I.R. (cm$^{-1}$) film: | 3430, [OH]; 3180 [NH]; 1765, 1710  [NCNC; CCH$_3$] |
| N.M.R. (τ, CDCl$_3$): | 7.9, s, 3H, [COCH$_3$]; |
| | 7.6, brm, 6H, [CH$_2$COCH$_3$; CH$_2$CH=CHCH$_2$]; |
| | 6.5, brm, 2H, [NCH$_2$]; |
| | 5.9, m, 1H, [NCH]; |
| | 4.6, m, 2H, [CH=CH]. |
| Mass Spec; C$_{22}$H$_{36}$N$_2$O$_3$(M*—H$_2$O) | requires 376.2724 |
| | found: 376.2711. |

EXAMPLE 8

Compound 8 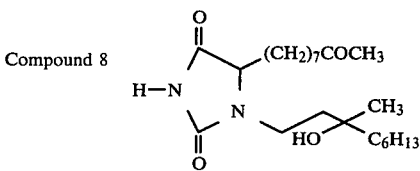

In a similar manner, Compound 8, 1-(3'-hydroxy-3'-methyl-n-nonyl)-5-(8''-oxo-n-nonyl) hydantoin was obtained from ethyl 2-[N-(3'-hydroxy-3'-methyl-n-nonyl)-N-aminocarbonyl]amino-10-oxo-undecanoate.

| | |
|---|---|
| I.R. (cm$^{-1}$) film: | 3430 [OH]; 3170 [NH]; 1770, 1710  [NCNC; CCH$_3$]. |
| N.M.R. (τ): | 7.85, s, 3H, [COCH$_3$]; |
| | 7.55, t, 2H, [CH$_2$COCH$_3$]; |
| | 6.7, brm, 2H, [NCH$_2$]; |
| | 5.95, m, 1H, [NCH]. |
| Mass Spec: C$_{22}$H$_{40}$N$_2$O$_4$(M*) | requires 396.2987 |
| | found 396.2978. |

EXAMPLE 9

Compound 9 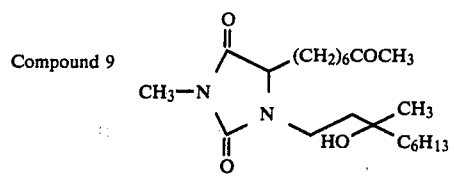

In a similar manner to that of Example 1(g), Compound 9, 1-(3'-hydroxy-3'-methyl-n-nonyl)-3-methyl-5-(7''-oxo-n-octyl) hydantoin was prepared from ethyl 2-(3'-hydroxy-3'-methyl-n-nonyl)amino-9-oxo-decanoate and methyl isocyanate.

| | |
|---|---|
| I.R. (cm$^{-1}$): film | 3450, [OH]; 1770, 1710 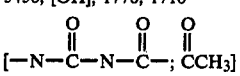 [—N—C—N—C—; CCH$_3$] |
| N.M.R. (τ): | 7.95, s, 3H, [COCH$_3$]; |
| | 7.65, m, 2H, [CH$_2$COCH$_3$]; |
| | 7.15, s, 1H, [OH]; |
| | 7.10, s, 3H, [NCH$_3$]; |
| | 6.6, brm, 2H, [NCH$_2$]; |
| | 6.0, m, 1H, [NCH]. |
| Mass Spec: C$_{22}$H$_{40}$N$_2$O$_4$(M*) | requires 396.2985 |
| | found 396.2981. |

EXAMPLE 10

Compound 10 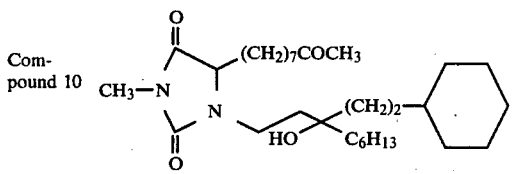

In a similar manner to that of Example 1(g), Compound 10, 1-(3'-hydroxy-3'-methyl-5'-cyclohexyl-n-pentyl)-3-methyl-5-(8''-oxo-n-nonyl) hydantoin was prepared from ethyl 2-(3'-hydroxy-3'-methyl-5'-cyclohexyl-n-pentyl)amino-10-oxo-undecanoate and methyl isocyanate.

ANALYSIS: C$_{25}$H$_{44}$N$_2$O$_4$ requires: C, 68.77; H, 10.16; N, 6.42%. found: C, 68.37; H, 10.38; N, 6.13%.

| | |
|---|---|
| I.R. (cm$^{-1}$) film: | 3450, [OH]; 1765, 1705 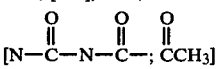 [N—C—N—C—; CCH$_3$] |
| N.M.R. (τ, CCl$_4$): | 7.95, s, 3H, [COCH$_3$]; |
| | 7.65, t, 2H, [CH$_2$COCH$_3$]; |
| | 7.45, s, 1H, [OH]; |
| | 7.05, s, 3H, [NCH$_3$]; |
| | 6.6, brm, 2H, [NCH$_2$]; |
| | 6.05, m, 1H, [NCH]. |
| Mass Spec: C$_{25}$H$_{44}$N$_2$O$_4$(M*) | requires 436.3297 |
| | found 436.3331. |

EXAMPLE 11

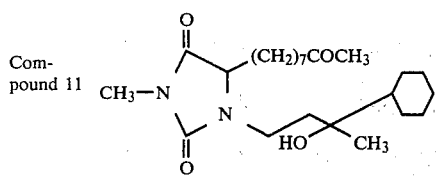

In a similar manner to that of Example 1(g), compound 11, 1-(3'-hydroxy-3'-cyclohexyl-n-butyl)-3-methyl-5-(8''-oxo-n-nonyl) hydantoin was prepared using ethyl 2-(3'-hydroxy-3'-cyclohexyl-n-butyl)amino-10-oxo-undecanoate and methyl isocyanate.

| | |
|---|---|
| I.R. (cm$^{-1}$): film | 3450 [OH]; 1765, 1705 [N—C—N—C; C—CH$_3$]. |
| N.M.R. ($\tau$, CDCl$_3$): | 7.85, s, 3H, [COCH$_3$]; |
| | 7.6, t, 2H, [CH$_2$COCH$_3$]; |
| | 7.45, s, 1H, [OH]; |
| | 7.0, s, 3H, [NCH$_3$]; |
| | 6.6, brm, 2H, [NCH$_2$]; |
| | 5.95, t, 1H, [NCH]. |
| Mass Spec: C$_{23}$H$_{38}$N$_2$O$_3$(M*—H$_2$O) requires | 390.2882 |
| found | 390.2876 |

PHARMACOLOGICAL DATA SECTION

1. Bronchodilator Activity (a) The Compounds were examined for their ability to inhibit 5-hydroxytryptamine induced bronchoconstriction in the anaesthetised, artificially respired guinea-pig (Konzett-Rossler preparation).

The results obtained are shown in the Table 1.

(b) The Compounds were also examined for their ability to protect conscious guinea-pigs against broncho-constriction induced by an histamine aerosol (Herxheimer test). The Compounds were administered by aerosol.

The results obtained are shown in the Table 1.

The aerosol was produced in the following manner.

Water soluble Compounds were dissolved in normal saline at a concentration of 1 μg/ml. Water insoluble Compounds were dissolved in ethanol at a concentration of 10 μg/ml. These solutions were then diluted to the test concentrations with normal saline.

TABLE 1

| Compound No | Konzett-Rossler Test Ed$_{50}$ μg/kg i.v. | % Increase in pre-convulsive coughing time at a dose of 10 μg/ml |
|---|---|---|
| 1 | 1.4 | NT |
| 6 | NT | 29% after 2 mins. 15% after 5 mins. |
| 8 | NT | 81% after 2 mins. |
| 9 | 67.5 | NT |
| 11 | 1.0 | 140% after 2 mins. 23% after 5 mins. |

2. Anti-Ulcer Activity

The compounds were examined for their ability to inhibit indomethacin induced gastric ulceration in the rat and the activities are shown in Table 2.

TABLE 2

| Compound | Dose mg/kg p.o. | % Inhibition of Damage |
|---|---|---|
| 1 | 100 | 100 |
| | 50 | 74 |
| | 25 | 64 |
| 2 | 100 | 100 |
| 3 | 100 | 65 |

TOXICITY

No toxic effects were observed in the tests reported above.

What we claim is:

1. A compound selected from the group consisting of a hydantoin derivative of the formula:

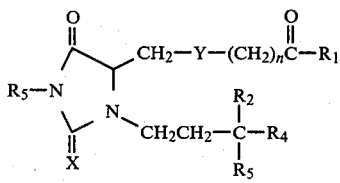

wherein
X is O, S or H$_2$;
Y is —CH$_2$CH$_2$—, —CH═CH— or —C≡C—;
n has a value of 1 to 7;
R$_1$ is alkyl of 1 to 4 carbon atoms;
R$_2$ is hydrogen or alkyl of 1 to 4 carbon atoms;
R$_3$ is hydroxy, alkanoyloxy of 1 to 4 carbon atoms or benzyl;
R$_4$ is alkyl of 1 to 9 carbon atoms, cycloalkyl of 3 to 8 carbon atoms or alkyl of 1 to 6 carbon atoms substituted with cycloalkyl of 3 to 8 carbon atoms, or
R$_2$ and R$_4$, together with the carbon atom to which they are attached, are cycloalkylidene of 5 to 8 carbon atoms; and
R$_5$ is hydrogen or alkyl of 1 to 6 carbon atoms; and the pharmaceutically acceptable acid addition salts thereof when X is H$_2$.

2. A compound according to claim 1 wherein n is 1 to 5.

3. A compound according to claim 2 wherein n is 4.

4. A compound according to claim 2 wherein X is O.

5. A compound according to claim 2 wherein Y is —CH$_2$—CH$_2$—.

6. A compound according to claim 2 wherein R$_1$ is methyl.

7. A compound according to claim 2 wherein R$_1$ is ethyl.

8. A compound according to claim 2 wherein R$_2$ is hydrogen.

9. A compound according to claim 2 wherein R$_2$ is methyl.

10. A compound according to claim 2 wherein R$_3$ is hydroxy.

11. A compound according to claim 2 wherein R$_4$ is alkyl of 4 to 9 carbon atoms.

12. A compound according to claim 11 wherein R$_4$ is n-pentyl, n-hexyl or n-heptyl.

13. A compound according to claim 12 wherein R$_4$ is n-hexyl.

14. A compound according to claim 11 wherein R$_4$ is hex-2-yl, hept-2-yl or oct-2-yl.

15. A compound according to claim 2 wherein $R_4$ is cyclohexyl.

16. A compound according to claim 2 wherein $R_5$ is hydrogen.

17. A compound according to claim 2 wherein $R_5$ is methyl.

18. A compound according to claim 1 wherein $R_2$ is hydrogen, methyl or ethyl, $R_3$ is hydroxy and $R_4$ is alkyl of 1 to 9 carbon atoms.

19. A compound according to claim 18 wherein X is O.

20. A compound according to claim 18 wherein Y is —$CH_2$—$CH_2$—.

21. A compound according to claim 18 wherein $R_1$ is methyl.

22. A compound according to claim 18 wherein $R_5$ is hydrogen.

23. A compound according to claim 18 wherein $R_5$ is methyl.

24. A compound according to claim 18 wherein $R_2$ is methyl.

25. A compound according to claim 18 wherein $R_4$ is alkyl of 4 to 9 carbon atoms.

26. A compound according to claim 25 wherein $R_4$ is n-pentyl, n-hexyl or n-heptyl.

27. A compound according to claim 26 wherein $R_4$ is n-hexyl.

28. A compound according to claim 25 wherein $R_4$ is hex-2-yl, hept-2-yl or oct-2-yl.

29. A compound according to claim 1 wherein $R_2$ is hydrogen, methyl or ethyl, $R_3$ is hydroxy and $R_4$ is cycloalkyl of 5 to 8 carbon atoms or alkyl of 1 to 6 carbon atoms substituted with cycloalkyl of 5 to 8 carbon atoms.

30. A compound according to claim 29 wherein X is O.

31. A compound according to claim 29 wherein Y is —$CH_2$—$CH_2$—.

32. A compound according to claim 29 wherein $R_1$ is methyl.

33. A compound according to claim 29 wherein $R_5$ is hydrogen.

34. A compound according to claim 29 wherein $R_5$ is methyl.

35. A compound according to claim 29 wherein $R_2$ is methyl.

36. A compound according to claim 29 wherein $R_4$ is cycloalkyl of 5 to 8 carbon atoms.

37. A compound according to claim 36 wherein $R_4$ is cyclohexyl.

38. A compound according to claim 29 wherein $R_4$ is alkyl of 1 to 4 carbon atoms substituted with cyclohexyl.

39. A pharmaceutical composition for effecting a prostaglandin-like effect comprising an effective amount of a compound according to claim 1 in combination with a pharmaceutically acceptable composition.

40. A method for the treatment in humans or animals of conditions responsive to natural prostaglandins, which comprises administering to a human or animal in need thereof an effective amount of a compound according to claim 1.

* * * * *